(12) United States Patent
Inoue et al.

(10) Patent No.: US 7,795,176 B2
(45) Date of Patent: Sep. 14, 2010

(54) ADSORBENTS FOR ADVANCED GLYCATION ENDPRODUCTS

(75) Inventors: Hiroyoshi Inoue, Kurume (JP);
Masayoshi Takeuchi, Takaoka (JP);
Shoichi Yamagishi, Kurume (JP)

(73) Assignee: Kurume University, Fukuoka (JP)

( * ) Notice: Subject to any disclaimer, the term of this patent is extended or adjusted under 35 U.S.C. 154(b) by 0 days.

(21) Appl. No.: 11/992,752

(22) PCT Filed: Sep. 29, 2006

(86) PCT No.: PCT/JP2006/320042
§ 371 (c)(1),
(2), (4) Date: Feb. 11, 2009

(87) PCT Pub. No.: WO2007/037554
PCT Pub. Date: Apr. 5, 2007

(65) Prior Publication Data
US 2009/0143226 A1    Jun. 4, 2009

(30) Foreign Application Priority Data
Sep. 30, 2005    (JP) ............................. 2005-286941

(51) Int. Cl.
*B01J 20/26*    (2006.01)
*B01J 20/22*    (2006.01)
*C08F 26/02*    (2006.01)
*C08F 26/06*    (2006.01)
*C08F 226/02*    (2006.01)
*C08F 226/06*    (2006.01)
*C08F 22/10*    (2006.01)
*C08F 218/14*    (2006.01)
*C08F 222/10*    (2006.01)

(52) U.S. Cl. ...................... 502/402; 502/401; 526/263; 526/320; 526/321

(58) Field of Classification Search ................ 502/401, 502/402; 526/263, 320, 321
See application file for complete search history.

(56) References Cited

FOREIGN PATENT DOCUMENTS

| | | |
|---|---|---|
| JP | 2004-300153 | 10/2004 |
| JP | 2005-139414 | 6/2005 |
| WO | 02/076443 A1 | 10/2002 |

OTHER PUBLICATIONS

Bedair et al., "Affinity chromatography with monolithic capillary columns II. Polymethacrylate monoliths with immobilized lectins for the separation of glycoconjugates by nano-liquid affinity chromatography." J. Chromatography A, 1079 (Mar. 2005) 236-245.*

(Continued)

*Primary Examiner*—Timothy C Vanoy
*Assistant Examiner*—Daniel Berns
(74) *Attorney, Agent, or Firm*—Wenderoth, Lind & Ponack, L.L.P.

(57) ABSTRACT

The object of the present invention is to provide an adsorbent having an excellent AGEs adsorption ability. The present invention provides an adsorbent for advanced glycation end products consists of a copolymer resin having hydrophilic methacrylate, wherein the constituent unit of said copolymer resin consists of a particular methacrylate compounds and vinyl compounds. Preferably, the copolymer resin having hydrophilic methacrylate has one or more basic ion-exchange groups.

14 Claims, 2 Drawing Sheets

OTHER PUBLICATIONS

Masayoshi Takeuchi et al., "*Immunological Detection of a Novel Advanced Glycation End-Product*", Molecular Medicine, vol. 7, No. 11, pp. 783-791 (2001).

Hiroyoshi Inoue et al., "*Design of a New Phosphate Binder, Anion Exchange Resin, Based on Microcalorimeter Measurements*", Letters in Drug Design & Discovery, vol. 2, No. 3, pp. 250-254 (2005).

* cited by examiner

ADSORBENTS FOR ADVANCED GLYCATION ENDPRODUCTS

TECHNICAL FIELD

The present invention relates to adsorbents which specifically adsorb advanced glycation end products (AGEs), respectively.

BACKGROUND ART

Advanced glycation end products (AGEs) are cross-linked polymers irreversibly formed by a series of reactions starting from a nonenzymatic reaction between carbonyl groups of reducing sugars such as glucose and amino groups of proteins (i.e. Maillard reaction). These reactions are gradually proceed in a living body over a long period. For example, hemoglobin AlC (HbAlc), a kind of AGEs, which is one of laboratory test indicators of diabetes is a glycation product of hemoglobin that is a protein of erythrocyte.

AGEs are causative substance of diabetes complications such as diabetic retinopathy and diabetic nephropathy. AGEs are also known to be associated with a crisis of diabetic angiopathy through binding to a specific receptor (RAGE) on vascular endothelial cells. Considering the report which indicates that in Japan, now, the number of patients potentially suffered form diabetes is increased up to 16,300,000 and in particular, one person per 4.5 middle-aged and older persons is in a prestage of a diabetes, removing AGEs from the living body is a very important for preventing crisis and progression of diabetes complication in the future. In addition, AGEs are associated with a crisis of debilitating disease such as atherosclerosis, Alzheimer's disease and arthritis rheumatoides.

Various kinds of drugs are proposed for removing AGEs from the human body. For example, so far, aminoguanidine derivatives and pyridoxamine derivatives have been known as inhibitors of AGEs formation. In addition, JP-A-2004-300153 have declared 3-methyl-1-phenyl-2-pyrazoline-5-on as the inhibitor. Although those inhibitors of AGEs formation are effective for preventing further accumulation of AGEs, those can not resolve a problem that is to remove already accumulated AGEs.

On the other hand, substances such as N-phenacylthiazolium bromide (PTB) which can break an established AGE-linkage have been studied. Recently, seven compounds including 1,4-benzene-bis[4-methyleneaminophenoxyisobutyric acid] that have the function are reported (e.g. JP-A-2004-529126). The AGE-degradation activities of those substances, however, are not sufficiently potent.

So far, any drugs which are effective for the elimination of accumulated AGEs has not been developed.

The present inventor developed a copolymer resin comprising hydrophilic methacrylate and found that the resin has an excellent ability to adsorb phosphoric acid and oxalic acid (see JP-A-2005-13.9414). Any use of the resin other than the above adsorption ability, however, is still not known.

DISCLOSURE OF INVENTION

An object of the present invention is to provide an adsorbent having an excellent ability to adsorb AGEs which are causative substance of diabetes complication.

An adsorbent for advanced glycation end products of the present invention comprises a copolymer resin having hydrophilic methacrylate, wherein the constituent unit of said copolymer resin is represented by the following formula [I]:

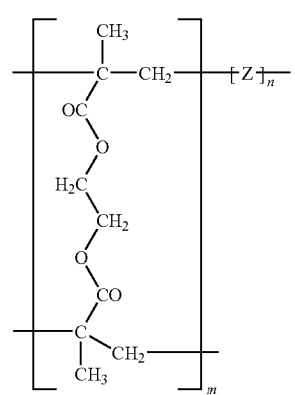

wherein Z is a substituted ethylene group represented by

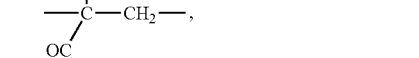

each of m and n represents number of monomer molecules, wherein the ratio of m to n is 0.1:99.9-15:85;

in the formula (Z1), Y is a pyridyl group or nitrogen atom-containing group represented by the following formula:

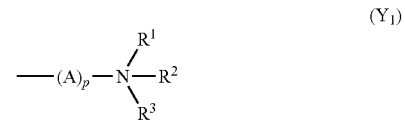

in the formula ($Y_1$), A is a carbonyl group, alkylene group having from 1 to 8 carbon atoms, arylene group or aralkylene group; p is 0 or 1; $R^1$, $R^2$ and $R^3$ are independently selected from hydrogen, alkyl group having from 1 to 4 carbon atoms and substituted alkyl group having from 1 to 4 carbon atoms, with the proviso that $R^1$, $R^2$ and $R^3$ are not hydrogen at the same time; when N is a quaternary ammonium, the counter ion may be present;

in the formula (Z2), $Y_1$ is a nitrogen atom-containing group represented by the above described formula ($Y_1$); and in the formula (Z3), $R^4$ is an alkyl group having from 1 to 4 carbon atoms.

In one embodiment, said copolymer resin having hydrophilic methacrylate has one or more basic ion-exchange groups.

In another embodiment, said copolymer resin having hydrophilic methacrylate is coated with one or more polymers.

In a further embodiment, said polymer comprises a 2-hydroxyethyl methacrylate polymer or a glycosideethyl methacrylate polymer.

In other embodiments, said copolymer resin having hydrophilic methacrylate comprises: ethyleneglycol dimethacrylate cross linking N-methylpyridylethylene hydrochloride copolymer, ethyleneglycol dimethacrylate cross linking N-methylpyridylethylene hydrochloride copolymer coated with 2-hydroxyethyl methacrylate-glycidyl methacrylate copolymer, ethyleneglycol dimethacrylate cross linking N-methylpyridylethylene hydrochloride copolymer coated with glycosideethyl methacrylate-glycidyl methacrylate copolymer, ethyleneglycol dimethacrylate cross linking 3-amino-2-hydroxypropylmethacrylate hydrochloride copolymer, or ethylene glycol dimetacrylate crosslinking triethylenetetramine-substituted glycidyl methacrylate copolymer.

The adsorbents for advanced glycation end products (AGEs) of the present invention have high abilities to adsorb AGEs, respectively. Said ability has an advantage which can not be found in other resins, especially in anion-exchange resin. The present adsorbents, for example, are useful as a medicine for a disease associated with AGEs such as diabetes complication, atherosclerosis, Alzheimer's disease and arthritis rheumatoides; a hemodialysis column; a column for purifying and isolating AGEs; a column for removing AGEs from a food; a column for removing a color from a food; and a cosmetic.

BEST MODE FOR CARRYING OUT THE PRESENT INVENTION

Figure 1:
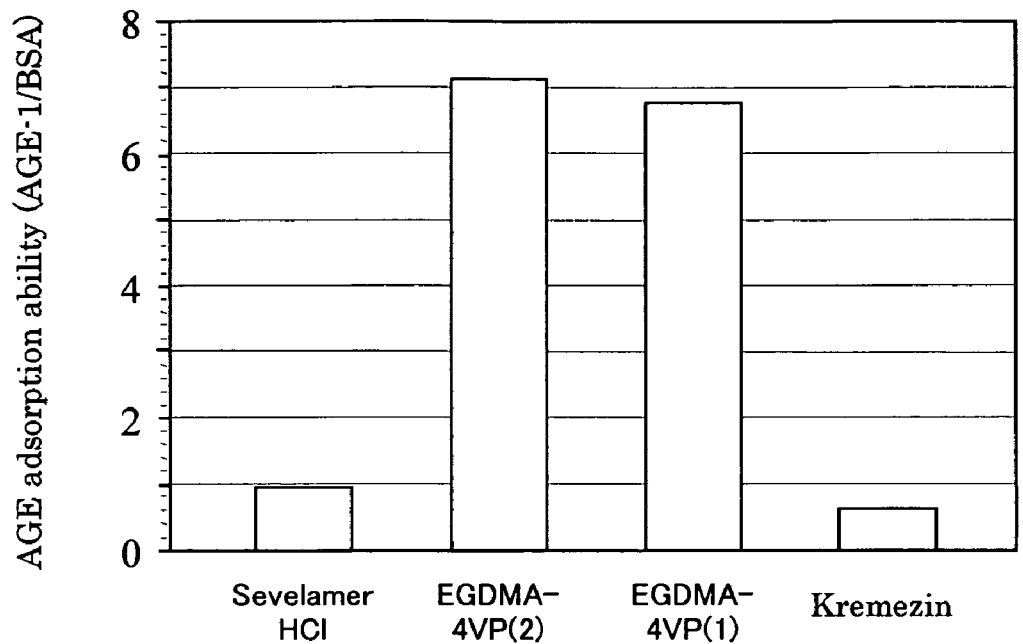
FIG. 1 shows ability of the adsorbent of the present invention and other resins to adsorb AGE-1.

The adsorbent for advanced glycation end products (AGEs) of the present invention comprises copolymer resin having hydrophilic methacrylate (hereinafter referred to as copolymer resin). Alternatively, the adsorbent comprises copolymer resin coated with one or more polymer.

The copolymer resin, the coated copolymer resin with a polymer and the adsorbents for AGEs comprising said copolymers are explained as follows, respectively.

(Copolymer Resin)

The constituent unit of copolymer resin used in the present invention is represented by the following formula [I]:

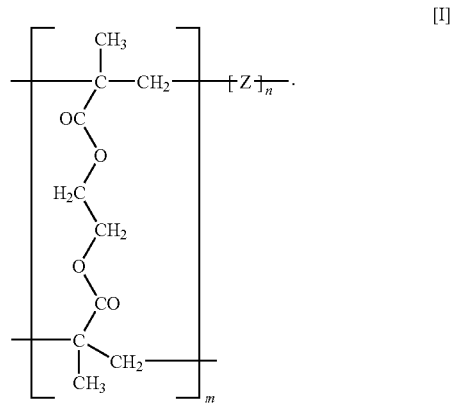

[I]

The copolymer may be random copolymer, block copolymer or graft copolymer.

In the above described formula [I], the substituted ethylene group Z is represented by one of the formulae (Z1)-(Z3):

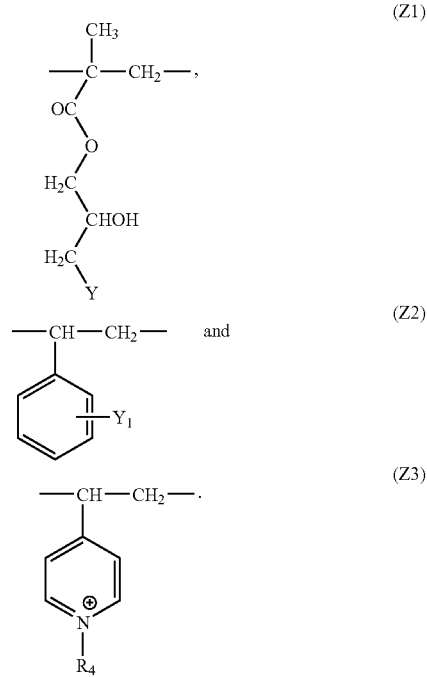

In the above described formula (Z1), Y is a pyridyl group or a nitrogen atom-containing group. The pyridyl group may have one or more substituent group. For example, the pyridyl group may be substituted by an alkyl group having from 1 to 4 carbon atoms such as methyl group, or hydroxyl group.

The above described nitrogen atom-containing group Y is represented by the following formula ($Y_1$):

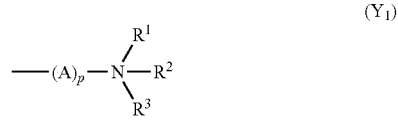

($Y_1$)

wherein A is a carbonyl group, alkylene group having from 1 to 8 carbon atoms, arylene group or aralkylene group; p is 0 or 1; $R^1$, $R^2$ and $R^3$ are independently selected from hydrogen, alkyl group having from 1 to 4 carbon atoms and substituted alkyl group having from 1 to 4 carbon atoms, with the proviso that $R^1$, $R^2$ and $R^3$ are not hydrogen at the same time; when N is a quaternary ammonium, the counter ion may be present.

In the above described formula ($Y_1$), alkyl group or substituted alkyl group which have from 1 to 4 carbon atoms, represented by $R^1$, $R^2$ and $R^3$ respectively, may be straight-chain or branched and includes, for example, methyl group, ethyl group, propyl group, butyl group, isopropyl group, hydroxymethyl group and hydroxyethyl group.

In the above described formula ($Y_1$), the nitrogen atom-containing group may be a tertiary amine or a quaternary ammonium. In the present invention, a quaternary ammonium is preferable. Due to the basic ion-exchange group in the copolymer, the amount of AGEs adsorbed by the copolymer is increased.

Examples of formula ($Y_1$) comprise the following nitrogen atom-containing groups: $-N(CH_3)_2$, $-N^+(CH_3)_3$, $-N(CH_3)_2 \ CH_2CH_2OH$, $-CONH(CH_2)_n \ N(CH_3)_2$ (wherein n is an integer from 1 to 5) and $-CH_2NH(CH_2CH_2NH)_n H$ (wherein n is an integer from 1 to 5).

In the above described formula (Z2), $Y_1$, is the nitrogen atom-containing group represented by the above described formula ($Y_1$).

In the above described formula (Z3), $R^4$ is an alkyl group having from 1 to 4 carbon atoms and may be a linear alkyl group or a branched alkyl group including, for example, methyl group, ethyl group, propyl group, butyl group and isopropyl group.

In the above described formula [I], m and n respectively represent number of monomer molecule of each constituent unit of the copolymer resin. The ratio of m to n is 0.1:99.9-15:85, preferably 2:98-12:88, more preferably 5:95-10:90, still more preferably 7:93-9:91, most preferably about 8:92. When the above described mole ratio is out of the range of 0.1:99.9-15:85, for example, when the mole ratio of m is less than 0.1, a substituted ethylene group is difficult to be incorporated into the copolymer resin and the resulting resin will have less AGEs adsorption ability. When the above described mole ratio is larger than 15, the intermolecular cross-linking will not proceed sufficiently and the resulting resin will be very rigid due to the poor matrix formation. The resin will hardly adsorb AGEs because the inside of the resin cannot be used for the adsorption.

Among the above described copolymer resins, ethylene glycol dimethacrylate-N-methylpyridylethylene copolymer (EGDMA-4VP) is preferably used because of the high AGEs adsorption ability.

The copolymer resin used in the present invention preferably has one or more basic ion-exchangeable group because of the high AGEs adsorption ability of the resulting resin. As described above, in the copolymer resin, each substituted ethylene group has a nitrogen atom. Thus, a strong basic ion-exchangeable group can be introduced by the conversion of the nitrogen atom to the quaternary ammonium. The ethylene glycol dimethacrylate-N-methylpyridylethylene hydrochloride copolymer (EGDMA-4VP hydrochloride), which is produced by a conversion of the above described EGDMA-4VP to the quaternary ammonium hydrochloride salt thereof, is preferably used in particular.

The copolymer resin of the present invention, for example, can be prepared by reacting a hydrophilic methacrylate compound and a vinyl compound, which can be monomers constituting the above described copolymer resin, in a dispersion medium for the polymerization. In addition, addition of amine and conversion of the amine to the quaternary ammonium may be conducted, if necessary. A method for synthesizing the copolymer resin used in the present invention is explained as follows.

Examples of the above described hydrophilic methacrylate compounds include hydroxyalkyl(meta)acrylates, alkoxyalkyl(meta)acrylates, amino(meta)acrylates, alkylamino(meta)acrylates, and poly(alkyleneglycol) (meta)acrylates. Ethyleneglycol dimethacrylate (EGDMA) is preferably used.

Examples of the above described vinyl compounds include vinyl chloride, vinyl acetate, maleic acid, acrylic acid, methacrylic acid, acrylamide, N-alkylacrylamide, styrenesulfonic acid, N,N-dimethylaminoethylacrylate, acryloylmorpholine, N,N-dimethylaminopropylacrylamide, hydroxyethylmethacrylate, N-vinyl pyrolidone, 2-acrylamide-2-methyl-propanesulfonic acid, glycidyl methacrylate (GMA) and 4-vinylpyridine (4-VP). 4-vinylpyridine (4-VP) is preferable. When a vinyl compound comprising no nitrogen atom such as GMA is used, an attaching the amine to the polymer is conducted preliminarily or after polymerization by the addition reaction.

The above described dispersion medium for the polymerization is not particularly restricted. For example, hydroxyethyl cellulose aqueous solution may be used as the dispersion medium for the polymerization. If required, sodium sulfate or sodium chloride may be added to the dispersion medium for the polymerization.

In the above described polymerization reaction, the ratio of the hydrophilic methacrylate compound to the vinyl compound is appropriately determined within the range of m and n defined in the above described formula [I]. Preferably, the weight ratio is 1:99-99:1, more preferably 3:97-40:60, still more preferably 5:95-20:80. The reaction temperature and the reaction time also may be appropriately determined depending on kinds of the employed compounds and compositions of desired copolymer.

After completing the polymerization, if required, specifically in the case where a vinyl compound with no nitrogen atom is used, attach the amine to the polymer is conducted by addition reaction. The addition reaction is conducted using, for example, ammonia or triethylene tetramine according to conventional methods which those skilled in the art usually employ. In this way, the copolymer resin having hydrophilic methacrylate of the present invention can be prepared.

If required, the nitrogen atom in the prepared copolymer resin is converted to the quaternary ammonium compound so that a strong basic ion-exchangeable group is introduced into the copolymer. The conversion to the quaternary ammonium compound is made, for example, by reacting the above described copolymer resin with bromomethane. The ratio of the above described copolymer resin to bromomethane may be appropriately determined depending on the ratio of introduction of the strong basic ion-exchangeable group to be introduced and is not particularly restricted. Preferably, the ratio of mass of the above described copolymer resin to bromomethane is 100:1-1:1, more preferably 50:1-5:1, still more preferably about 10:1. The prepared copolymer resin, if desired, is converted to the hydrochloric salt using hydrochloric acid.

(Coating of Copolymer Resin with One or More Polymers)

The above described copolymer resin is preferably coated with one or more polymers. In particular, by coating the copolymer resin with one or more polymers having higher hydrophilicity than the copolymer resin, a gastrointestinal burden in the case of administrating the resin into the body will be reduced. In addition, the coating facilitates mixing of the resin with food in the stomach (See H. Inoue and S.

Yamagishi, Letters in Drug Design & Discovery, 2005, Vol. 2, No. 3, page 250-254). Examples of polymers with high hydrophilicity include polymers of 2-hydroxyethyl methacrylate (HEMA), glycosideethyl methacrylate (GEMA) and glycidyl methacrylate (GMA). These polymers may be used solely, or in a combination of two or more. Further, a copolymer of these polymers may be used. Examples of the copolymer include GMA-HEMA copolymer and GMA-GEMA copolymer.

The coating is carried out according to the method which those skilled in the art conventionally employs. For example, the coating is conducted by soaking the copolymer resin into the solution containing the above described polymer (e.g. DMSO solution, aqueous solution) then after drying it.

(Adsorbent for AGEs)

The adsorbent of the present invention for AGEs comprises the above described copolymer resin. In particular, it preferably comprises ethyleneglycol dimethacrylate cross-linking N-methylpyridylethylene hydrochloride copolymer, ethylene glycol dimethacrylate cross-linking N-methylpyridylethylene hydrochloride copolymer coated with 2-hydroxyethyl methacrylate-glycidyl methacrylate copolymer, ethylene glycol dimethacrylate cross-linking N-methylpyridylethylene hydrochloride copolymer coated with glycosideethyl methacrylate-glycidyl methacrylate copolymer, ethylene glycol dimethacrylate cross-linking 3-amino-2-hydroxypropylmethacrylate hydrochloride copolymer, or ethylene glycol dimethacrylate cross-linking triethylenetetramine-substituted glycidyl methacrylate copolymer. The adsorbent for AGEs has a high ability of adsorbing AGEs, which can not be found in other resins including anion-exchange resin. Particularly, introduction of basic ion-exchangeable groups to the copolymer resin can prepare an adsorbent with higher AGEs adsorption ability.

The adsorbent for AGEs of the present invention, for example, is useful for manufacturing a medicine for a disease associated with AGEs such as diabetes complication, atherosclerosis, Alzheimer's disease and arthritis rheumatoides; a hemodialysis column; a column for purifying and isolating AGEs; a column for removing AGEs from a food; a column for removing a color from a food; and a cosmetic.

AGEs which are adsorbed by the adsorbent for AGEs of the present invention are those usually known by those skilled in the art and they are not restricted specifically. AGEs include, for example, AGE-1 and AGE-2 as defined in, for example, Takeuchi et al., Mol. Med., 7, 783 (2001), pentosidine, clostrin, X1 (fluorolink), pyrropyridine, pyrraline, carboxymethyl lysine, imidazolone compounds, carboxyethyl lysine, methyl glyoxal dimer, glyoxal dimer, imidazolidine and arg-pyrimidine.

When the adsorbent for AGEs of the present invention is used as a medicine, the adsorbent may usually be administered orally, via a gavage or enterally (rectal administration). In the case of oral administration, it may be administered as a formulation of capsule, tablet, powder (dispersant), granule or suspension.

When the adsorbent for AGEs of the present invention is used for a medicine, it is preferable that the dosage is given so that 10 mg-200 mg/kg body weight is administered to the adult per day. The administration of less than 10 mg/kg body weight may not sufficiently exert the efficacy. The administration of more than 200 mg/kg body weight may stress the intestine.

When the adsorbent for AGEs of the present invention is used for a column filler for chromatogram, the amount used and the mode for use are not restricted. For example, the column packed with the adsorbent may be used in the hemodialysis system for chronic and acute dialysis patients. The columns may be arranged in series in the flow of the systems. Alternatively, the column may be used for removing AGEs from food or removing color from food, where food in liquid form or liquid component of food is applied to the column packed with the adsorbent.

When the adsorbent for AGEs of the present invention is used for cosmetics, the adsorbent may be pulverized and added to the beauty cream formulation.

EXAMPLES

Example 1

Preparation of Ethylene Glycol Dimethacrylate Cross-Linking N-Methylpyridylethylene (EGDMA-4VP) Hydrochloride Copolymer (1) and Evaluation of the Ages Adsorption Ability (1) Reagents Ethylene glycol dimethacrylate (EGDMA; the extra-pure grade reagent, Wako Pure Chemical Industries, Ltd., Japan) was subjected to the polymerization reaction after removing the polymerization inhibitor by means of washing with 10% aqueous sodium hydroxide. Before applying to the polymerization reaction, EGDMA was stored in a container the atmosphere in which was replaced with nitrogen. 4-vinylpyridine (4VP; Wako Pure Chemical Industries, Ltd., Japan) was used after distillation under reduced pressure. A polymerization initiator, azobisisobutyronitrile (AIBN; the guarantee reagent grade, Wako Pure Chemical Industries, Ltd., Japan), was used without any preliminary treatment.

(2) Preparation of Dispersion Media for Polymerization

A dispersion media for polymerization was prepared by adding sodium chloride to 0.5 w/v % aqueous hydroxyethyl cellulose so that the final concentration of sodium chloride is 10 w/v %.

(3) Synthesis 500 mL of the dispersion media for polymerization was added into a separable 3-necked round-bottom flask (1000 mL) equipped with a thermometer, a stirrer having two stirring blades (blade diameter: 80 mm) made of Teflon (registered trademark), a dimroth condenser, and a channel for argon supply. Under a nitrogen atmosphere, the solution was stirred at 400 rpm for about 10 minutes, followed by adjusting the stirring speed at 300 rpm. Then, 100 mg of AIBN was dissolved in 100 mL of a mixture of EGDMA and 4-VP, in which the mass ratio is 80:20, to prepare a monomer mixture and the mixture was then added to the dispersion media for polymerization.

After confirming that the spherical monomer phase is appropriately dispersed in the dispersion media for polymerization using an optical microscope, the temperature was increased to 70° C. over 30-40 minutes and the polymerization was conducted for 4 hours with keeping the temperature at 70° C. Further, the temperature was raised to 80° C. and the reaction was conducted for 1 hour at 80° C. The reaction product was then obtained after gradually cooling over more than 5 hours. The reaction product was filtrated by suction, and washed three times with hot deionized water and further, with a mixture of equal parts of deionized water and methanol, followed by drying at 60° C. for 12 hours. The resulting product was dried during the day and night under reduced pressure to prepare ethylene glycol dimethacrylate cross-linking N-methylpyridylethylene copolymer.

The resulting copolymer was reacted with bromomethane. Then, the reaction product was washed with a mixture of equal parts of ionized water and methanol and dried to prepare the polymer having quaternary ammonium in free base form.

The elemental analysis of the polymer in free base form was conducted to determine the nitrogen content. About 5 g of the polymer in free base form was added in a beaker (100 mL) and was sufficiently swollen by adding deionized water followed by adding 1N hydrochloric acid in an amount corresponding to 40 mol % of the determined nitrogen content with stirring by a glass rod. The mixture was left standing at room temperature over more than one night. After that, the conversion to hydrochloride salt was confirmed by checking that the pH of supernatant of the suspension was 5-6, and that no white turbidity was found after adding 0.1M silver nitrate to the supernatant. Further, resulting product was washed with a mixture of equal parts of ionized water and methanol and dried sufficiently to prepare ethylene glycol dimethacrylate cross-linking N-methylpyridylethylene hydrochloride copolymer (hereinafter referred to as EGDMA-4VP (1)) represented by the following formula:

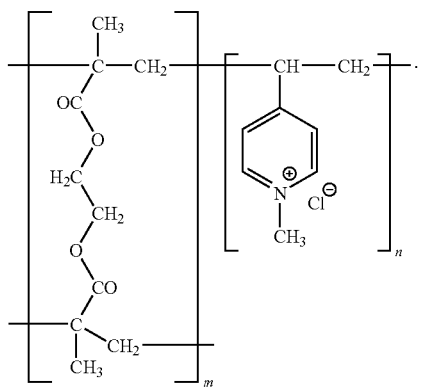

Analysis of resulting EGDMA-4VP (1) using elemental analyzer (MT-700HCN, yanaco, Japan) shows carbon: 57.81%, hydrogen: 6.70%, and nitrogen: 1.98%. The low nitrogen content represented that less amount of substituents corresponding to 4-VP was introduced into the EGDMA-4VP (1).

(4) Evaluation of the Ages Adsorption Ability 50 mM phosphate buffer (pH 7.4) containing each about 200 μg/mL of bovine serum albumin (BSA) and AGE-1 (as defined in Takeuchi et al., Mol. Med., 7, 783 (2001)) was added to a tube. Before adding the resin, AGE-1 content was determined by ELISA using anti-AGE-1 polyclonal antibody (kindly gifted by Professor Masayoshi Takeuchi of Hokuriku University, faculty of pharmaceutical sciences) and total protein content (i.e. sum of AGE-1 content and BSA content) was determined by the Lowry method. Then, 50 mg of EGDMA-4VP (1) prepared in the above described (3) was added to the mixture followed by stirring with rotation at 37° C. for 3 hours. After stirring, centrifugation at 3000 rpm for 3 minutes was conducted to prepare the supernatant. AGE-1 content and total protein content of the supernatant were determined. Each of the adsorbed amount of AGE-1 and the total adsorbed amount of protein were determined by subtracting the content determined after adding the resin from the content determined before adding the resin, respectively. In addition, the adsorbed amount of BSA was calculated by subtracting the adsorbed amount of AGE-1 from the adsorbed amount of total protein. The ability of the resin to adsorb AGE-1 was evaluated based on the following formula:

AGE adsorption ability=Amount of adsorbed AGE-1/Amount of adsorbed BSA.

The result is shown in FIG. 1.

Figure 2:
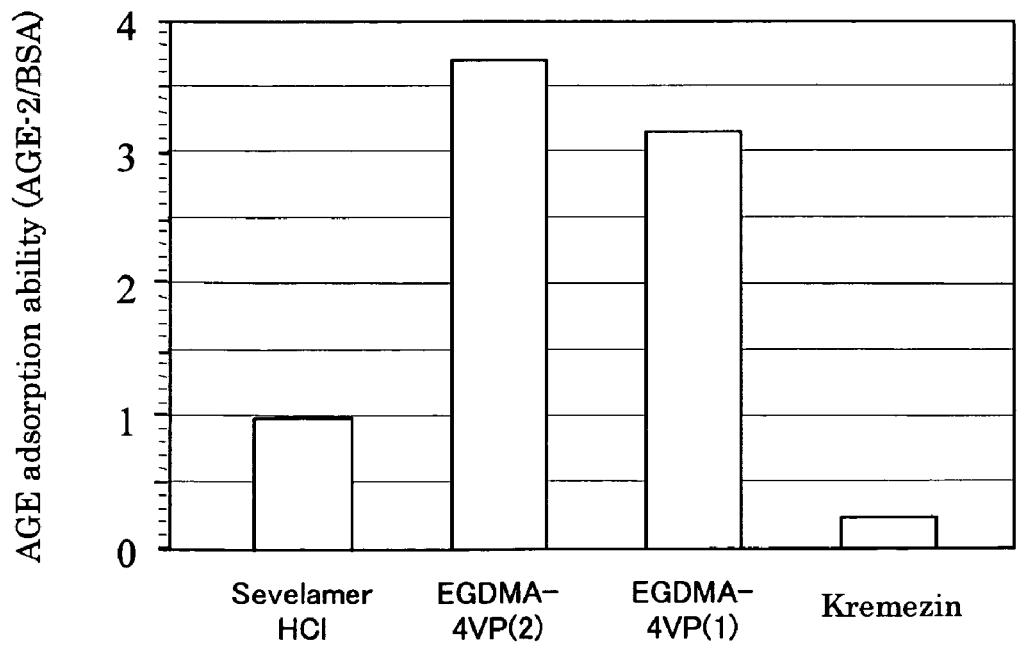
FIG. 2 shows ability of the adsorbent of the present invention and other resins to adsorb AGE-2.

Then, the ability of EGDMA-4VP (1) to adsorb AGE-2 was evaluated in accordance with a procedure similar to that described above except AGE-2 (as defined in Takeuchi et al., Mol. Med., 7, 783 (2001)) was used in place of AGE-1 and anti-AGE-2 polyclonal antibody (kindly gifted by Professor Masayoshi Takeuchi of Hokuriku University, faculty of pharmaceutical sciences) was used in place of anti-AGE-1 polyclonal antibody. The result is shown in FIG. 2.

Example 2

Preparation of EGDMA-4VP Hydrochloride Copolymer (2) and Evaluation of the Ages Adsorption Ability of the Same Ethylene glycol dimethacrylate cross-linking N-methylpyridylethylene hydrochloride copolymer (2) (hereinafter referred to as EGDMA-4VP (2)) was prepared in accordance with a procedure similar to Example 1 except the mass ratio of EGDMA to 4-VP was 10:90. Analysis of resulting EGDMA-4VP (2) using elemental analyzer (MT-700HCN, yanaco, Japan) shows carbon: 53.10%, hydrogen: 6.83%, and nitrogen: 8.94%. It was found that the nitrogen content was higher compared to EGDMA-4VP (1) (more than 4 fold) and many substituents corresponding to 4-VP were introduced into the copolymer. Using the EGDMA-4VP (2), the AGE-1 adsorption ability and the AGE-2 adsorption ability were evaluated similar to Example 1. The results are shown in FIG. 1 and FIG. 2, respectively.

Comparative Examples 1 and 2

The ability to adsorb AGE-1 and AGE-2 was evaluated in accordance with a procedure similar to Example 1 except each of Sevelamer HCl (anion-exchange resin; Kirin Brewery Company, Limited, Japan) and Kremezin (charcoal having activated surface form (non-specific adsorption); Sankyo, Limited, Japan) were used in place of EGDMA-4VP (1) (hereinafter referred to as Comparative examples 1 and 2, respectively). The results are shown in FIG. 1 and FIG. 2, respectively.

As shown in FIGS. 1 and 2, both EGDMA-4VP (1) and (2) prepared in Example 1 and 2 have higher ability to adsorb each of AGE-1 and AGE-2 than the resins used in Comparative examples 1 and 2. Those results show that the adsorbent of the present invention specifically adsorbs AGEs and has a high AGE adsorption ability. In addition, from the results showing that EGDMA-4VP (1) having substituents corresponding to 4-VP at the low rate as prepared in Example 1 exhibits predominant AGEs adsorption ability, it can be understood that the AGEs adsorption ability results from specific capture of AGE in the formed matrices of resin. EGDMA-4VP hydrochloride copolymer resin (EGDMA-4VP (2)) as prepared in Example 2 has particularly high AGEs adsorption ability.

Example 3

Coating of EGDMA-4VP Hydrochloride Copolymer 1

A copolymer of 2-hydroxyethyl methacrylate (HEMA; the extra pure grade reagent, Wako Pure Chemical Industries, Ltd., Japan) and glycidyl methacrylate (GMA; Nacalai tesque, Ltd., Japan) was prepared as a polymer for coating as follows. First of all, those reagents were distilled under reduced pressure to remove the polymerization inhibitor (hydroxy monomethyl ether). Then, 12 mL of HEMA and 60 μL of GMA in 50 mL of ethanol were polymerized at 60° C. for ten hours in the presence of 400 mg of α,α'-azobisisobutyronitrile (polymerization initiator; Nacalai tesque, Ltd., Japan). The obtained GMA-HEMA copolymer was added dropwise into acetone to give spherical beads and collected by filtration. Then, the obtained beads were dried under reduced pressure and crushed using mill to prepare a powder of GMA-HEMA copolymer.

10 g of the resulting powder of GMA-HEMA copolymer was dissolved in 50 mL of dimethylsulfoxide (DMSO). Into the resulting solution, 20 g of EGDMA-4VP hydrochloride copolymer (EGDMA-4VP (1)) prepared in Example 1 was added, sufficiently soaked followed by filtration and drying in air and further, in a vacuum drier at 120° C. to prepare a coated EGDMA-4VP (1). The resulting GMA-HEMA coated EGDMA-4VP (1) has the same AGEs adsorption ability with the uncoated one.

Example 4

Coating of EGDMA-4VP Hydrochloride Copolymer 2

A powder of GMA-GEMA copolymer was prepared in accordance with a procedure similar to Example 3 except glucoside ethylmethacrylate (GEMA; Nippon Fine Chemical Co., Ltd., Japan) was used in place of HEMA. Then, EGDMA-4VP (1) coated with GMA-GEMA copolymer was prepared in accordance with a procedure similar to Example 3. The resulting GMA-GEMA coated EGDMA-4VP (1) has the same AGEs adsorption ability with the uncoated one.

Example 5

Preparation of EGDMA Cross-Linking 3-Amino-2-Hydroxypropyl Methacrylate (AHPMA) Hydrochloride Copolymer

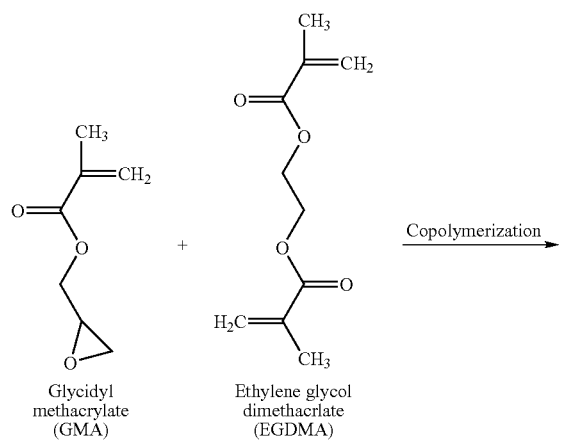

Glycidyl methacrylate (GMA)   Ethylene glycol dimethacrlate (EGDMA)

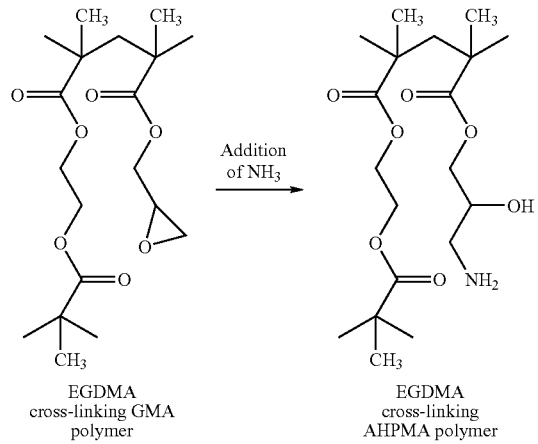

EGDMA cross-linking GMA polymer   EGDMA cross-linking AHPMA polymer (1) Reagents EGDMA (the extra pure grade reagent, Wako Pure Chemical Industries, Ltd., Japan) was subjected to the polymerization reaction after removing the polymerization inhibitor by means of washing with 10% aqueous sodium hydroxide. Before the polymerization reaction, EGDMA was stored in a container the atmosphere in which was replaced with nitrogen. Glycidyl methacrylate (GMA; the extra pure grade, Wako Pure Chemical Industries, Ltd., Japan) was used after distillation under reduced pressure. A polymerization initiator, azobisisobutyronitrile (AIBN; the guarantee reagent grade, Wako Pure Chemical Industries, Ltd., Japan), was used without any preliminary treatment.

(2) Preparation of Dispersion Media for Polymerization

A dispersion media for polymerization was prepared by mixing 6 g of sodium sulfate (the guarantee reagent grade, Nacalai tesque, Ltd., Japan) into 50 mL of aqueous solution comprising 1 w/v % of hydroxyethyl cellulose (Tokyo Chemical Industry Co., Ltd., Japan) (4500-6000 cps) followed by adding deionized water up to 500 mL of the total volume.

(3) Synthesis 500 mL of the dispersion media for polymerization was added into a separable 3-necked round-bottom flask (1000 mL) equipped with a thermometer, a stirrer having two stirring blades (blade diameter: 80 mm) made of Teflon (registered trademark), a dimroth condenser, and a channel for nitrogen supply. Under a nitrogen atmosphere, the solution was stirred at 400 rpm for about 10 minutes, followed by adjusting the stirring speed at 250 rpm.

Then, 28.5 g of GMA, 1.5 g of EGDMA and 100 mg of AIBN were mixed and the resulting mixture was added into the dispersion media for polymerization.

After confirming that the spherical monomer phase is appropriately dispersed in the dispersion media for polymerization using an optical microscope, the temperature was increased to 50° C. over about 1 hour and the polymerization was conducted for 2 hours with keeping the temperature 50° C. Then after, the temperature was raised to 80° C. over 30 minutes and the reaction was conducted for 1 hour. The reaction product was collected by suction filtration and washed three times with hot deionized water and further, with methanol. Then, the resulting product was dried at 60° C. for 12 hours and further, in a desiccator under reduced pressure over night.

Then, 30 mL of ethanol was added in a pressure-resistant reaction container (200 mL) which was sufficiently cooled by dry ice-acetone bath, and ammonia gas was injected for about 20 minutes into the container. 10 g of the dried product as prepared above was added in the pressure-resistant reaction container and after shaking it, the reaction was conducted in a water bath at 60° C. for 10 hours. After the container was opened after cooling in the dry ice-acetone bath, the reaction product was transferred into deionized water and left standing in a draft until unreacted ammonia was evaporated. The reaction product was put into a glass column tube and washed with a mixture of equal parts of deionized water and methanol until the pH of the outflow fluid was 6-7 and further, washed with methanol. Then, it was dried at 60° C. for 12 hours and further, in a desiccator under reduced pressure for about 12 hours. The obtained polymer was confirmed to be EGDMA-AHPMA copolymer after determination of infrared absorption spectrum of it using DR-8000 (SHIMADZU CORPORATION, Japan, 3FT01).

In addition, a hydrochloride salt of the copolymer was prepared as follows. First of all, elemental analysis of the resulting EGDMA-AHPMA copolymer was conducted and thereby nitrogen content was determined. 4.8 g of said copolymer was added in a beaker (100 mL) and was sufficiently swollen by adding deionized water followed by adding 1N hydrochloric acid in an amount of corresponding to 40 mol % of the determined nitrogen content with stirring by a glass rod. The volume of added hydrochloric acid was 7.02 mL. The mixture was left standing at room temperature for about 12 hours. After that, the conversion to hydrochloride salt was confirmed by checking that the pH of supernatant of the suspension was 5-6, and that no white turbidity was found after adding 0.1M silver nitrate to the supernatant. Then after, the resulting product was put in a glass column tube and washed with methanol. Then, it was dried at 60° C. for 12 hours and further, in a desiccator under reduced pressure for about 24 hours to obtain EGDMA-AHPMA hydrochloride copolymer. Then, copolymer, particle diameter of which is less than or equal to 710 μm was collected using a filter having No. 24 mesh as defined by JIS.

Example 6

Preparation of EGDMA Cross-Linking 3-amino-2-hydroxypropyl Methacrylate (AHPMA) Hydrochloride Copolymer EGDMA-AHPMA hydrochloride copolymer was prepared in accordance with a procedure similar to Example 5 except 27.0 g of GMA and 3.0 g of EGDMA were used. The volume of added 1N hydrochloric acid was 7.30 mL per 4.99 g of copolymer.

Example 7

Preparation of EGDMA Cross-Linking Triethylenetetramine Substituted Glycidyl Methacrylate (TTA Substituted GMA) Copolymer

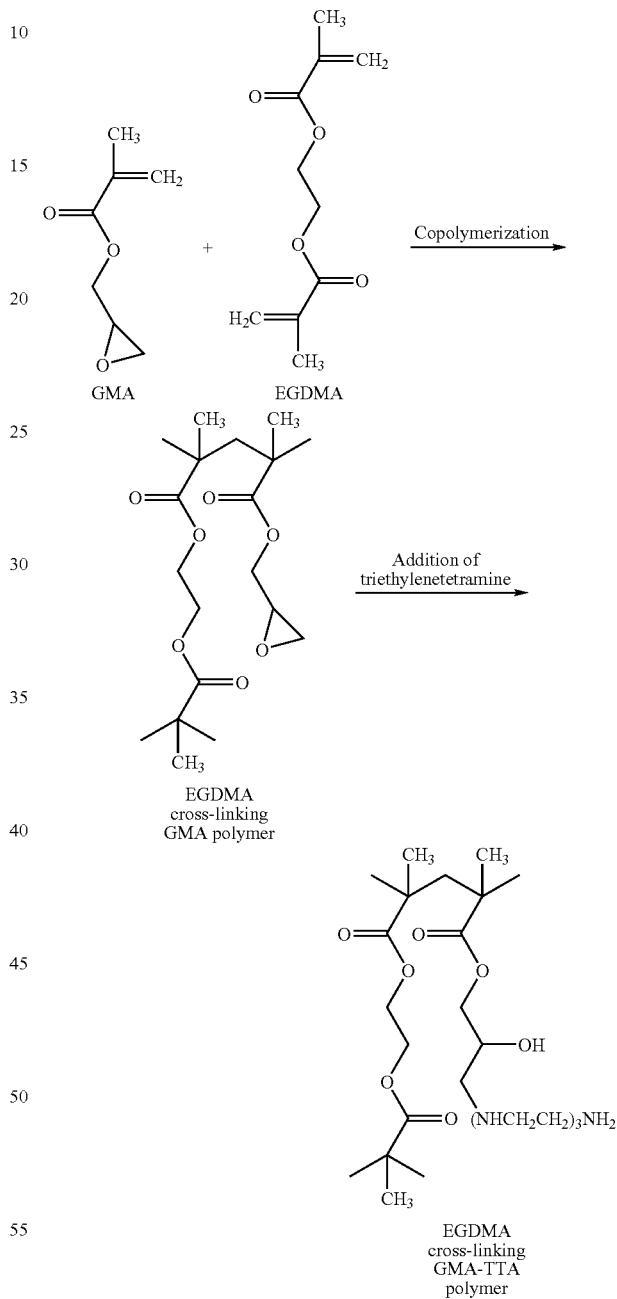

(1) Reagents

EGDMA was subjected to the polymerization reaction after removing the polymerization inhibitor by means of washing with 10% aqueous sodium hydroxide. GMA was used after distillation under reduced pressure (6 mmHg, 76° C.). A triethylenetetramine (TTA; the extra pure grade, Wako Pure Chemical Industries, Ltd., Japan) was used after distillation under reduced pressure. A polymerization initiator AIBN was used without any preliminary treatment. Before subjecting to the polymerization reaction, EGDMA and GMA were stored in a container the atmosphere in which was replaced with nitrogen.

(2) Preparation of Dispersion Media for Polymerization

A dispersion media for polymerization was prepared by mixing 6 g of sodium sulfate (the guarantee reagent grade, Nacalai tesque, Ltd., Japan) into 50 mL of aqueous solution comprising 1 w/v % of hydroxyethyl cellulose (Tokyo Chemical Industry Co., Ltd., Japan) (4500-6000 cps) followed by adding deionized water up to 500 mL of the total volume.

(3) Synthesis 500 mL of the dispersion media for polymerization was added into a separable 3-necked round-bottom flask (1000 mL) equipped with a thermometer, a stirrer having two stirring blades (blade diameter: 80 mm) made of Teflon (registered trademark), a dimroth condenser, and a channel for nitrogen supply. Under a nitrogen atmosphere, the solution was stirred at 400 rpm for about 10 minutes, followed by adjusting the stirring speed at 250 rpm.

Then, 29.4 g of GMA, 0.6 g of EGDMA and 100 mg of AIBN were mixed and the resulting mixture was added into the dispersion media for polymerization.

After confirming that the spherical monomer phase is appropriately dispersed in the dispersion media for polymerization using an optical microscope, the temperature was raised to 50° C. over about 1 hour and the polymerization was conducted for 2 hours with keeping the temperature 50° C. Further, the temperature was raised to 80° C. over 30 minutes and the reaction was conducted for 1 hour at 80° C. The reaction product was collected by suction filtration and washed three times with hot deionized water and further, with methanol. Then, the resulting product was dried at 60° C. for 12 hours and further, in a desiccator under reduced pressure over night.

About 30 g of the dried product was screened with shaking for 30 minutes by screening apparatus equipped with stacked filters having No. 22, No. 30, No. 42, No. 60, No. 83, No. 100, No. 140 and No. 200 as defined by JIS respectively, in order. The fractions between 100-42 mesh (149-355 μm) and the fractions between 42-30 mesh (355-500 μm) were collected and subjected to the following reaction.

5 g of the fractions as prepared above, 12.5 mL of TTA and 37.5 mL of 1,4-dioxane were added into the pressure-resistant reaction container (the volume of which is 200 mL) and after shaking it, the reaction was conducted in a water bath at 80° C. for 5 hours. After the container was opened, the reaction product was transferred into deionized water and the reaction product was collected by suction filtration. The reaction product was put into a glass column tube and washed with 0.1N aqueous hydrochloric acid and further, with 0.1N aqueous sodium hydroxide, followed by washing with deionized water until pH of the outflow fluid was 6-7. Further, the obtained reaction product was washed with methanol by means of aspiration using Buchner funnel equipped with 5B filter paper. Then, it was dried at 60° C. for 12 hours and further, in a desiccator under reduced pressure for about 12 hours. The obtained polymer was confirmed to be EGDMA-TTA substituted GMA copolymer after determination of infrared absorption spectrum of it using DR-8000 (SHIMADZU CORPORATION, Japan, 3FT01).

In addition, a hydrochloride salt of the copolymer was prepared as follows. First of all, elemental analysis of the resulting EGDMA-TTA substituted GMA copolymer was conducted and thereby nitrogen content was determined. About 2 g of said copolymer was added in a conical flask (50 mL) and was sufficiently swollen by adding deionized water followed by adding 1N hydrochloric acid in an amount corresponding to the determined nitrogen content with stirring by a glass rod. After the mixture was left standing at room temperature for about 12 hours, the reaction mixture was filtrated by suction using Buchner funnel equipped with 5B filter paper. Then, it was dried at 60° C. for 12 hours and further, in a desiccator under reduced pressure for about 24 hours to obtain EGDMA-TTA substituted GMA hydrochloride copolymer.

Example 8

Preparation of EGDMA Cross-Linking Triethylenetetramine Substituted Glycidyl Methacrylate (TTA Substituted GMA) Copolymer EGDMA-TTA substituted GMA hydrochloride copolymer was prepared in accordance with a procedure similar to Example 7 except 28.5 g of GMA and 1.5 g of EGDMA were used.

Example 9

Use of EGDMA-4VP (1) Resin for a Column (1) Preparation of AGE-2

180 mg of DL-glyceraldehyde (Wako Pure Chemical Industries, Ltd., Japan) and 39 mg of diethylenetriaminepentaacetic acid (chelating agent, Wako Pure Chemical Industries, Ltd., Japan) were added into a falcon tube (50 mL). Then 20 mL of 0.2 M phosphate buffer (pH 7.4) was added to said falcon tube and mixed by vortex mixer in order to be dissolved. The phosphate buffer used above was prepared as follows: 24 g/l (0.2M) sodium dihydrogen phosphate was added into a beaker and 95 mL of 28.39 g/L (0.2M) di-sodium hydrogen phosphate was further added to adjust the solution pH7.4 confirmed by pH meter. Then, 500 mg of bovine serum albumin (BSA; non-fatty acid-containing, Nacalai tesque, Ltd., Japan) was added to said falcon tube and dissolved using vortex mixer. After being dissolved, the sterile solution was prepared in a clean bench, by sterile filtration of the solution using a filter, pore size of which was 0.22 μm (made by Millipore Corporation). The falcon tube (50 mL), in which the sterile solution was put, was sealed with PARAFILM and incubated at 37° C. for 1 week. Then, the solution was applied to PD-10 column (GE Healthcare Bio-Sciences KK) in order to remove unreacted DL-glyceraldehyde and the eluate was confirmed by HPLC (made by Gilson, Inc.). Fractions in which AGE-2 was detected were collected and if necessary, the eluate was concentrated by dialysis to prepare AGE-2.

(2) Preparation of Anti-AGE-2 Monoclonal Antibody

A monoclonal antibody, antigen of which was AGE-2 as prepared in (1), was prepared using mice (The preparation was outsourced to TOYOBO Co. Ltd., Japan).

(4) Evaluation of Ages Adsorption Ability 5 mL of EGDMA-4VP (1) resin as prepared in Example 1 was packed in 5 mL column. 5 mL of anion-exchange resin DOWEX 50 W (The Dow Chemical Company) was similarly packed in another 5 mL column and used as a reference.

A whole blood derived from a SD rat (male, 10 weeks old) containing heparin sodium (Shimizu Pharmaceuticals Co. Ltd., Japan) was prepared. In the whole blood, AGE-2 as prepared in (1) was mixed to be the final concentration of 100 μg/mL. The column as prepared above was connected to a tube and 20 mL of the whole blood was applied to the column so that the flow speed was adjusted to be 1 mL/min by PERISTA pump (AS ONE corporation, Japan). The experiment was conducted at room temperature (20° C.). The blood sample which passed through the column was centrifuged at 3000 rpm for 5 minutes and only the supernatant was extracted.

AGE-2 ELISA was prepared using the monoclonal antibody as prepared in (2) and ELISA preparation kit (Nacalai tesque, Ltd., Japan). Using the ELISA, AGE-2 concentration of each of samples before or after passing through the column was determined. In addition, total protein concentration contained in each of the samples was determined according to the Lowry method.

Figure 3:
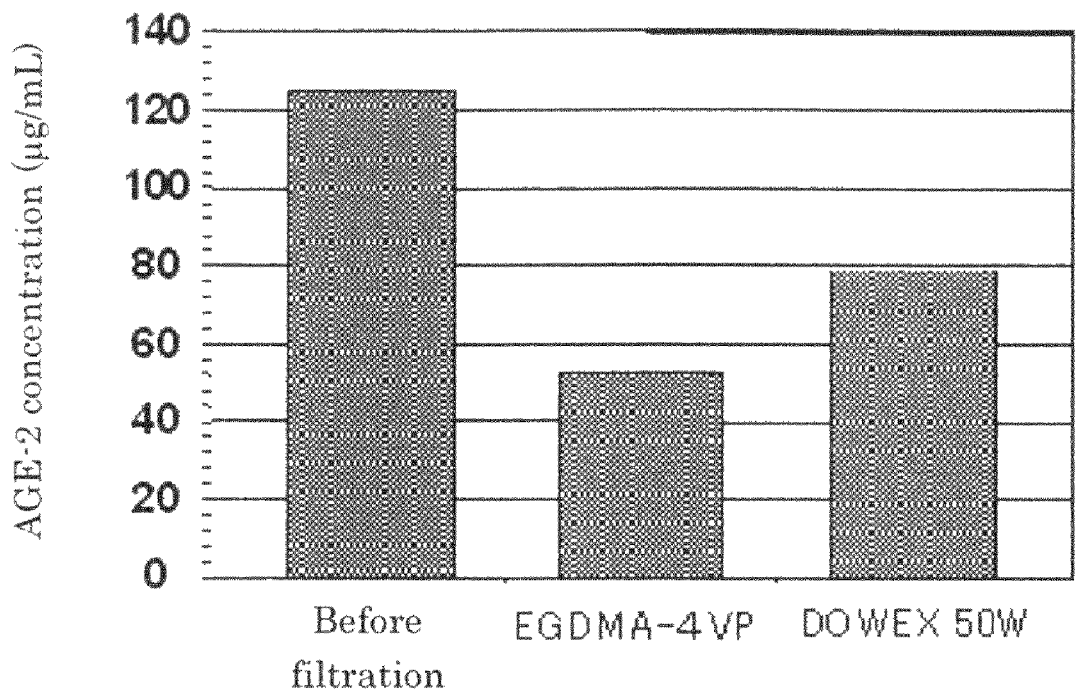
FIG. 3 shows a concentration of AGE-2 in the whole blood before and after filtration using a column packed with the adsorbent of the present invention or other resins.
Figure 4:
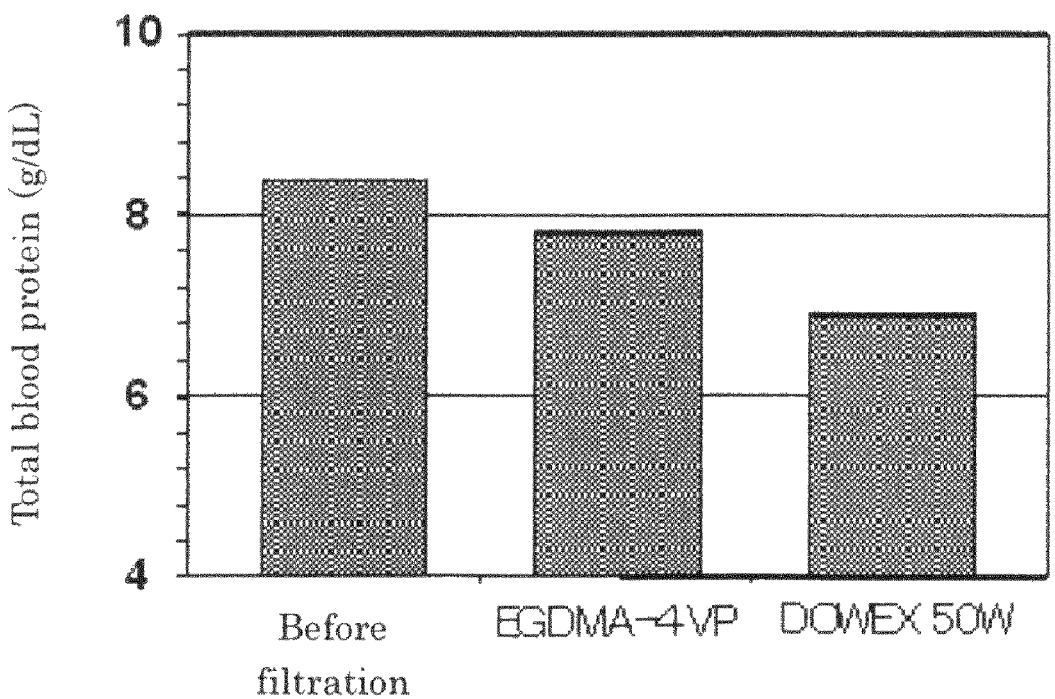
FIG. 4 shows a concentration of total protein in the whole blood before and after filtration using a column packed with the adsorbent of the present invention or other resins.

The AGE-2 concentration and the total blood protein concentration of the blood sample after passing through the column packed with the EGDMA-4VP (1) resin or anion-exchange resin DOWEX 50 W are shown in FIG. 3 and FIG. 4. As shown in FIG. 3 and FIG. 4, in the case of a column packed with anion-exchange resin DOWEX 50 W, both AGE-2 concentration and total blood protein concentration after filtration were reduced compared to those before filtration. On the other hand, in the case of a column packed with EGDMA-4VP (1) resin, AGE-2 concentration after filtration was remarkably reduced, but total blood protein concentration after filtration was not so reduced compared to those before filtration. From the results, it can be understood that a column packed with EGDMA-4VP (1) resin has a selective AGE-2 adsorption ability.

INDUSTRIAL APPLICABILITY

The adsorbent for advanced glycation end products (AGEs) of the present invention has a predominant AGEs adsorption ability. Such adsorption ability is an excellent effect which cannot be found in other resins including anion-exchange resins. The adsorbent is useful for manufacturing a medicine for a disease associated with AGEs such as diabetes complication, atherosclerosis, Alzheimer's disease and arthritis rheumatoides; a hemodialysis column; a column for purifying and isolating AGEs; a column for removing AGEs from a food; a column for removing a color from a food; and a cosmetic.

The invention claimed is:

1. A method for removing advanced glycation end products from a subject, said method comprising:

contacting a subject comprising advanced glycation end products with a copolymer resin comprising a hydrophilic methacrylate, wherein a constituent unit of the copolymer is represented by the following formula [I]:

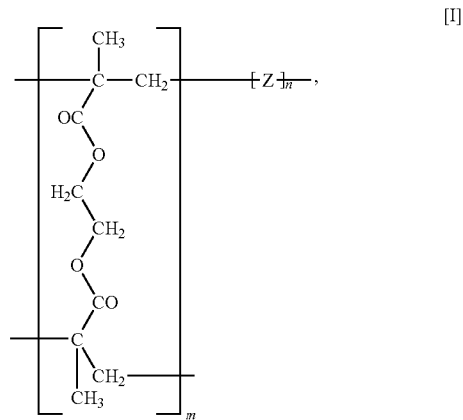

wherein Z is a substituted ethylene group represented by

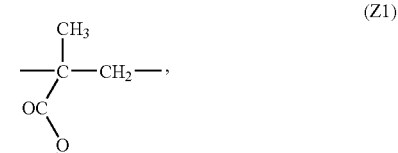

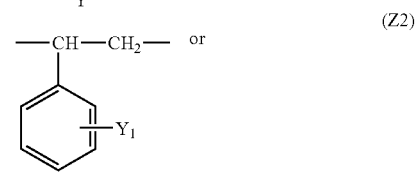

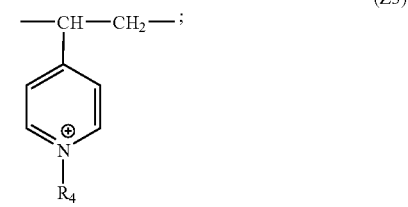

each of m and n represents a number of monomer molecules, wherein the ratio of m to n is 0.1:99.9-15:85; and in the formula (Z1), Y is a pyridyl group or a nitrogen atom-containing group represented by the following formula:

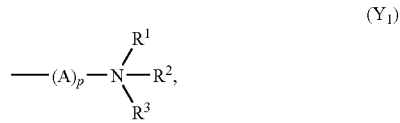

in the formula ($Y_1$), A is a carbonyl group, alkylene group having from 1 to 8 carbon atoms, arylene group or aralkylene group; p is 0 or 1; $R^1$, $R^2$ and $R^3$ are independently selected from the group consisting of hydrogen, an alkyl group having from 1 to 4 carbon atoms and a hydroxy alkyl group having from 1 to 4 carbon atoms, with the proviso that $R^1$, $R^2$ and $R^3$ are not hydrogen at the same time; and when N is a quaternary ammonium, a counter ion may be present;

in the formula (Z2), $Y_1$ is a nitrogen atom-containing group represented by the above described formula ($Y_1$); and in the formula (Z3), $R^4$ is an alkyl group having from 1 to 4 carbon atoms.

2. The method of claim 1, wherein the copolymer resin comprising a hydrophilic methacrylate has a basic ion-exchangeable group.

3. The method of claim 1, wherein the copolymer resin comprising a hydrophilic methacrylate is coated with a polymer.

4. The method of claim 3, wherein the polymer is 2-hydroxyethyl methacrylate polymer or glycosideethyl methacrylate polymer.

5. The method of claim 1, wherein the copolymer resin comprising a hydrophilic methacrylate is selected from the group consisting of an ethyleneglycol dimethacrylate cross-linking N-methylpyridylethylene hydrochloride copolymer, an ethylene glycol dimethacrylate cross-linking N-methylpyridylethylene hydrochloride copolymer coated with 2-hydroxyethyl methacrylate-glycidyl methacrylate copolymer, an ethylene glycol dimethacrylate cross-linking N-methylpyridylethylene hydrochloride copolymer coated with glycosideethyl methacrylate-glycidyl methacrylate copolymer, an ethylene glycol dimethacrylate cross-linking 3-amino-2-hydroxypropylmethacrylate hydrochloride copolymer, and an ethylene glycol dimethacrylate cross-linking triethylenetetramine-substituted glycidyl methacrylate copolymer.

6. The method of claim 2, wherein the copolymer resin comprising a hydrophilic methacrylate is coated with a polymer.

7. The method of claim 6, wherein the polymer is 2-hydroxyethyl methacrylate polymer or glycosideethyl methacrylate polymer.

8. The method of claim 1, wherein the subject is a human.

9. The method of claim 8, wherein the subject suffers from a disease or condition associated with advanced glycation end products.

10. The method of claim 8, wherein the disease or condition is selected from the group consisting of diabetes complication, atherosclerosis, Alzheimer's disease and arthritis rheumatoides.

11. The method of claim 1, wherein the subject is blood and the method comprises conducting hemodyalysis using a hemodyalysis column packed with the copolymer resin comprising a hydrophilic methacrylate.

12. The method of claim 1, wherein the subject is a food.

13. The method of claim 1, wherein the subject is a cosmetic.

14. A method for isolating and/or purifying advanced glycation end products, said method comprising:

contacting a sample comprising advanced glycation end products with a copolymer resin comprising a hydrophilic methacrylate, wherein a constituent unit of the copolymer is represented by the following formula [I]:

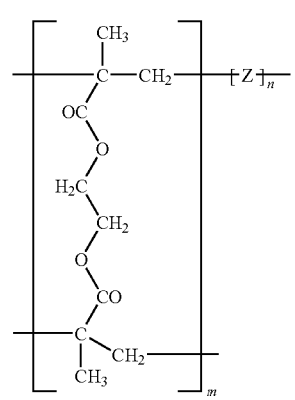

wherein Z is a substituted ethylene group represented by

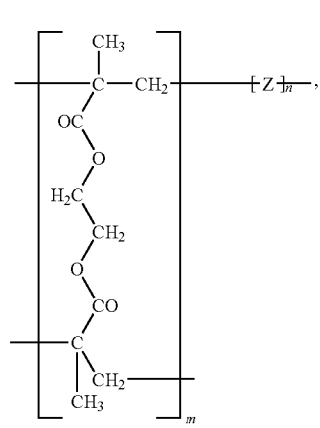

each of m and n represents a number of monomer molecules, wherein the ratio of m to n is 0.1:99.9-15:85; and in the formula (Z1), Y is a pyridyl group or a nitrogen atom-containing group represented by the following formula:

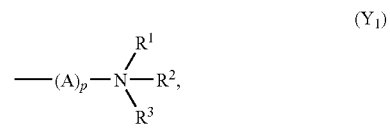

in the formula ($Y_1$), A is a carbonyl group, alkylene group having from 1 to 8 carbon atoms, arylene group or aralkylene group; p is 0 or 1; $R^1$, $R^2$ and $R^3$ are independently selected from the group consisting of hydrogen, an alkyl group having from 1 to 4 carbon atoms and a hydroxy alkyl group having from 1 to 4 carbon atoms, with the proviso that $R^1$, $R^2$ and $R^3$ are not hydrogen at the same time; and when N is a quaternary ammonium, a counter ion may be present;

in the formula (Z2), $Y_1$ is a nitrogen atom-containing group represented by the above described formula ($Y_1$); and in the formula (Z3), $R^4$ is an alkyl group having from 1 to 4 carbon atoms.

* * * * *